(12) United States Patent
Okuda

(10) Patent No.: US 11,135,102 B2
(45) Date of Patent: Oct. 5, 2021

(54) ABSORBENT ARTICLE FOR SECURELY ABSORBING BODY FLUID

(71) Applicant: DAIO PAPER CORPORATION, Ehime (JP)

(72) Inventor: Takashi Okuda, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 334 days.

(21) Appl. No.: 16/081,316

(22) PCT Filed: Feb. 24, 2017

(86) PCT No.: PCT/JP2017/007120
§ 371 (c)(1),
(2) Date: Aug. 30, 2018

(87) PCT Pub. No.: WO2017/169391
PCT Pub. Date: Oct. 5, 2017

(65) Prior Publication Data
US 2019/0083329 A1    Mar. 21, 2019

(30) Foreign Application Priority Data

Mar. 28, 2016   (JP) .............................. JP2016-064239

(51) Int. Cl.
*A61F 13/511*     (2006.01)
*A61F 13/535*    (2006.01)
(Continued)

(52) U.S. Cl.
CPC ........ *A61F 13/51121* (2013.01); *A61F 13/47* (2013.01); *A61F 13/472* (2013.01);
(Continued)

(58) Field of Classification Search
CPC .. A61F 13/47; A61F 13/472; A61F 13/51108; A61F 13/51121; A61F 13/512;
(Continued)

(56) References Cited

U.S. PATENT DOCUMENTS 3,881,491 A  *  5/1975 Whyte ..................... A61F 13/42
                                                        604/370
4,055,180 A  *  10/1977 Karami ................. A61F 13/536
                                                        604/368
(Continued)

FOREIGN PATENT DOCUMENTS

CN        2827323 Y      10/2006
GB        2181036        4/1987
(Continued)

OTHER PUBLICATIONS

International Search Report for PCT/JP2017/007120 dated May 23, 2017.
(Continued)

*Primary Examiner* — Michele M Kidwell
(74) *Attorney, Agent, or Firm* — IPUSA, PLLC

(57) ABSTRACT

A plurality of openings (11) is formed in a region corresponding to at least a body fluid discharge region (H) of a liquid permeable top sheet (3). A polymer sheet (6) disposed adjacent to a surface of an absorbent body (4) side of the liquid permeable top sheet (3) is included, and the polymer sheet includes highly absorbent resin disposed along a longitudinal direction on both sides of the region corresponding to the body fluid discharge region (H). Upon the highly absorbent resin becoming swollen by absorption, a space (10) for holding a body fluid is formed between regions in which the highly absorbent resin is disposed (12) and also between the liquid permeable top sheet (3) and the polymer sheet (6).

6 Claims, 8 Drawing Sheets

(51) Int. Cl.
| | |
|---|---|
| *A61F 13/512* | (2006.01) |
| *A61F 13/539* | (2006.01) |
| *A61F 13/472* | (2006.01) |
| *A61F 13/533* | (2006.01) |
| *A61F 13/537* | (2006.01) |
| *A61F 13/47* | (2006.01) |
| *A61F 13/45* | (2006.01) |

(52) U.S. Cl.
CPC ........ *A61F 13/512* (2013.01); *A61F 13/5123* (2013.01); *A61F 13/51108* (2013.01); *A61F 13/533* (2013.01); *A61F 13/535* (2013.01); *A61F 13/537* (2013.01); *A61F 13/539* (2013.01); *A61F 13/53747* (2013.01); *A61F 13/53752* (2013.01); *A61F 2013/4568* (2013.01); *A61F 2013/4708* (2013.01); *A61F 2013/53778* (2013.01)

(58) Field of Classification Search
CPC .. A61F 13/5123; A61F 13/533; A61F 13/535; A61F 13/537; A61F 13/53747; A61F 13/53752; A61F 13/539; A61F 2013/53778; A61F 2013/4568; A61F 2013/4708
See application file for complete search history.

(56) References Cited

U.S. PATENT DOCUMENTS

| | | | | |
|---|---|---|---|---|
| 4,676,785 A | * | 6/1987 | Battista | A61F 13/512 428/132 |
| 5,533,991 A | * | 7/1996 | Kirby | A61F 13/51305 604/383 |
| 5,575,785 A | * | 11/1996 | Gryskiewicz | A61F 13/49426 604/385.28 |
| 5,941,863 A | | 8/1999 | Guidotti et al. | |
| 6,175,056 B1 | * | 1/2001 | Carlucci | A61F 13/47227 604/369 |
| 7,404,810 B2 | * | 7/2008 | Toro | A61F 13/4755 604/367 |
| 7,956,236 B2 | * | 6/2011 | Ponomarenko | A61F 13/53713 604/378 |
| 9,035,127 B2 | * | 5/2015 | Nakajima | A61F 13/5323 604/382 |
| 2005/0148971 A1 | * | 7/2005 | Kuroda | A61F 13/512 604/380 |
| 2005/0256475 A1 | | 11/2005 | Komatsu et al. | |
| 2006/0058761 A1 | | 3/2006 | Kudo et al. | |
| 2006/0100598 A1 | * | 5/2006 | Tamura | A61F 13/4704 604/380 |
| 2007/0093164 A1 | * | 4/2007 | Nakaoka | A61F 13/536 442/385 |
| 2009/0270825 A1 | | 10/2009 | Wciorka et al. | |
| 2010/0198179 A1 | * | 8/2010 | Noda | A61F 13/536 604/365 |
| 2011/0313384 A1 | * | 12/2011 | Akiyama | A61F 13/53717 604/378 |

FOREIGN PATENT DOCUMENTS

| | | |
|---|---|---|
| JP | H8-191857 | 7/1996 |
| JP | H10-511582 | 11/1998 |
| JP | 2005-312526 | 11/2005 |
| JP | 2008-142220 | 6/2008 |
| JP | 2011-518613 | 6/2011 |
| JP | 2011-135979 | 7/2011 |
| JP | 2015-150057 | 8/2015 |
| WO | 1997/034559 | 9/1997 |
| WO | 2007/034451 | 3/2007 |
| WO | 2011/070728 | 6/2011 |

OTHER PUBLICATIONS

Extended European search report for European Patent Application No. 17773936.4 dated Mar. 4, 2019.
Office Action dated Sep. 18, 2020 issued with respect to the corresponding Chinese Patent Application No. 201780020079.6.

* cited by examiner

ABSORBENT ARTICLE FOR SECURELY ABSORBING BODY FLUID

TECHNICAL FIELD

The present invention relates to an absorbent article used for a sanitary napkin, a panty liner, an incontinence pad, or toiletry, and specifically relates to an absorbent article in which a polymer sheet including highly absorbent resin is disposed between a liquid permeable top sheet and an absorbent body, and a space for holding a body fluid is formed between the liquid permeable top sheet and the polymer sheet when the highly absorbent resin becomes swollen by absorption.

BACKGROUND ART

Conventionally, as an absorbent article such as a panty liner, a sanitary napkin, or an incontinence pad, an absorbent article that includes an absorbent body made of cotton-like pulp and interposed between a liquid impermeable back sheet such as a polyethylene sheet or a polyethylene-sheet-laminated non-woven fabric and a liquid permeable top sheet such as a non-woven fabric or a liquid permeable plastic sheet is known.

As a result of continuous improvements, a variety of absorbent articles that prevent body fluids from remaining on the surface as much as possible have been developed. For example, Patent Document 1 mentioned below discloses an absorbent article in which an absorbent body includes a fluid receiving space extending generally on a same plane. The receiving space includes one or more cavities or regions having density lower than density of a portion of the absorbent body, which is located adjacent to the receiving space. The receiving space is disposed in an absorbent body storage layer. The storage layer includes a material whose volume increases in a direction generally perpendicular to a first surface of the article when a portion of the storage layer becomes wet. Accordingly, as a result of the article becoming wet, the receiving space also increases in size in the direction perpendicular to the first surface of the article.

Further, Patent Document 2 mentioned below discloses an absorbent article in which a first passing layer formed of a resin film having fluid passing holes and a second passing layer formed of a resin film having fluid passing holes are layered on a fluid passing layer that covers the surface of a fluid absorbing layer. The second passing layer is configured to be collapsed more easily than the first passing layer.

RELATED-ART DOCUMENTS

Patent Documents

[Patent Document 1] Japanese Unexamined Patent Application Publication No. 10-511582
[Patent Document 2] Japanese Unexamined Patent Application Publication No. 2005-312526

SUMMARY OF THE INVENTION

Problem to be Solved by the Invention

In the case of panty liners and sanitary napkins among the above-described absorbent articles, thick menstrual blood with high viscosity or a clot of coagulated menstrual blood, which may remain on the surface of a typical non-woven fabric, may be discharged. If such menstrual blood with high viscosity remains on the surface, discomfort could be caused when the menstrual blood makes contact with the skin. Therefore, there has been a need to prevent menstrual blood from remaining on the surface of a liquid permeable top sheet.

In light of the above, in the absorbent article disclosed in Patent Document 1, when a non-woven fabric or a porous plastic film is used as a first liquid permeable casing sheet (a liquid permeable top sheet), there is a possibility that menstrual blood with high viscosity may remain on the surface. Also, when a surface sheet or the absorbent body is compressed by body pressure, there is also a possibility that body fluids that have passed through the liquid permeable top sheet and have been absorbed by the absorbent body may return back to the outer surface of the surface sheet.

Further, in the absorbent article disclosed in Patent Document 2, the surface sheet is formed of two passing layers. Therefore, even if menstrual blood with high viscosity can pass through the first passing layer, there may be a case in which the menstrual blood does not pass through the second passing layer and remains between the two layers. Also, there is a possibility that the menstrual blood remaining between the two layers may return back to the surface side when body pressure is applied. In view of the above, it is a general object of an embodiment of the present invention to provide an absorbent article that securely absorbs a body fluid with high viscosity while preventing the absorbed body fluid from returning back to the surface, and that also reduces discomfort when worn.

Means to Solve the Problem

According to one aspect, an absorbent article includes a liquid permeable top sheet including a plurality of openings in a region corresponding to at least a body fluid discharge region, a back sheet, and an absorbent body provided between the liquid permeable top sheet and the back sheet. The absorbent article also includes a polymer sheet disposed adjacent to a surface of an absorbent body side of the liquid permeable top sheet, and the polymer sheet includes highly absorbent resin disposed along a longitudinal direction on both sides of the region corresponding to the body fluid discharge region. When the highly absorbent resin becomes swollen by absorption, a space for holding a body fluid is formed between regions in which the highly absorbent resin is disposed and also between the liquid permeable top sheet and the polymer sheet.

Effects of the Invention

As described above, an absorbent article according to at least one embodiment of the present invention can securely absorb a body fluid with high viscosity while preventing the absorbed body fluid from returning back to the surface, and can also reduce discomfort when worn.

BRIEF DESCRIPTION OF THE DRAWINGS

FIGS. 3(A) and (B) are cross-sectional views of the sanitary napkin 1, in which FIG. 3(A) illustrates a state before excretion and FIG. 3(B) illustrates a state after excretion;

FIGS. 8(A) and (B) are cross-sectional views of the sanitary napkin 1, in which FIG. 8(A) illustrates a state before excretion and FIG. 8(B) illustrates a state after excretion; and FIGS. 9(A) and (B) are cross-sectional views of a sanitary napkin 1 according to a variation example, in which FIG. 9(A) illustrates a state before excretion FIG. 9(B) illustrates a state after excretion.

MODE FOR CARRYING OUT THE INVENTION

In the following, embodiments of the present invention are described below with reference to the accompanying drawings.

[Basic Structure of Sanitary Napkin 1]

Figure 1:
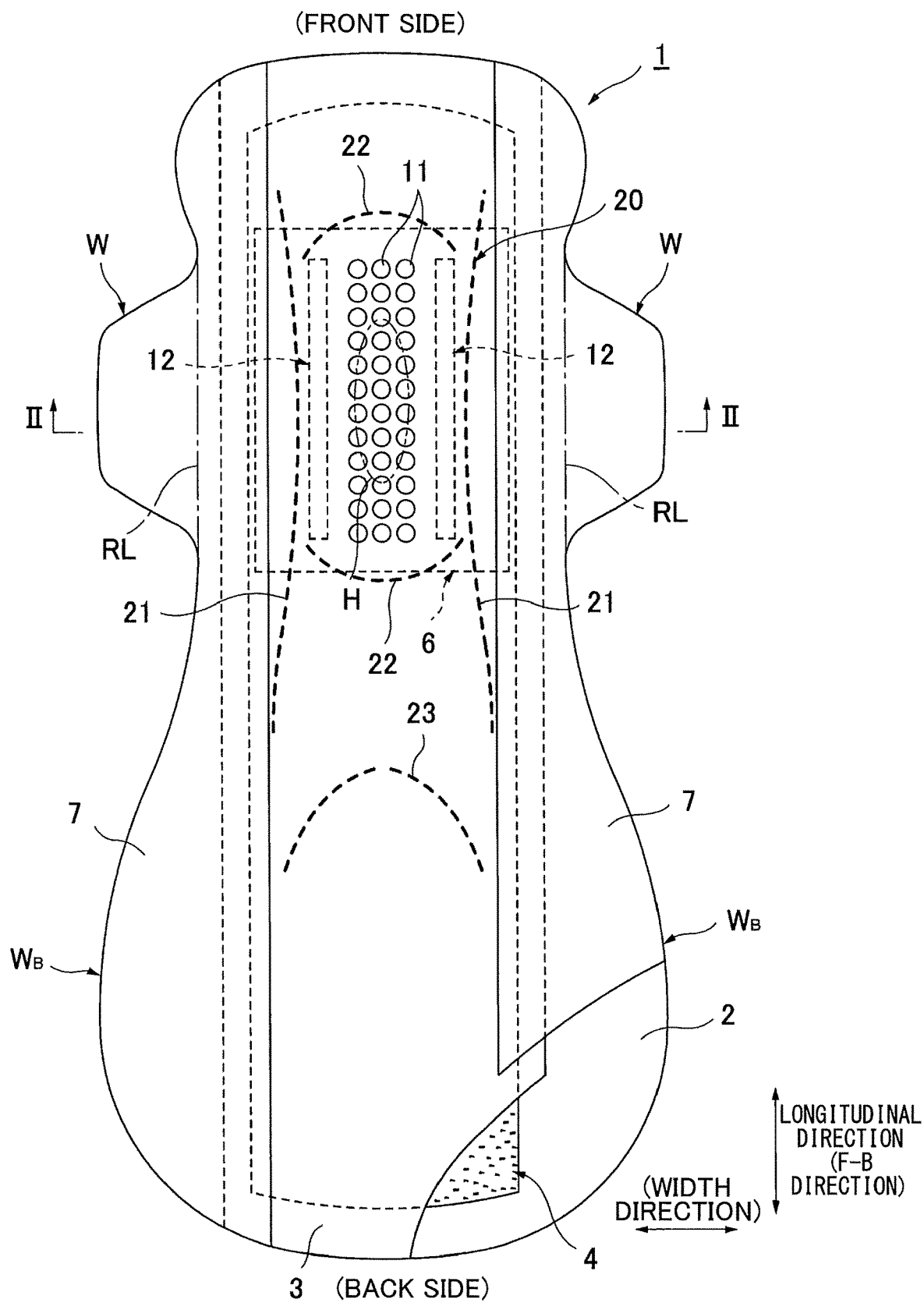
FIG. 1 is a partially expanded cutaway view of a sanitary napkin 1.
Figure 2:
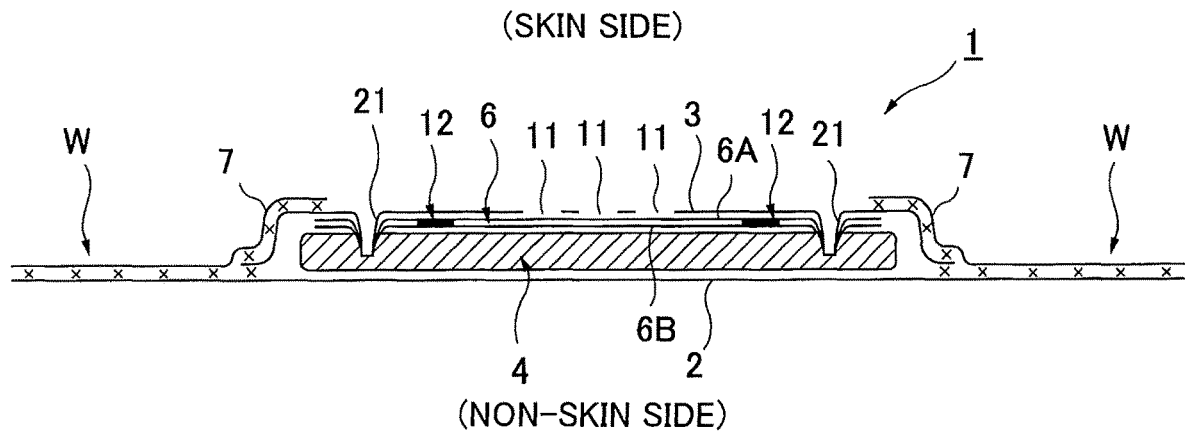
FIG. 2 is a cross-sectional view taken along a line II-II of FIG. 1 (a cross-sectional view of the sanitary napkin 1)

As illustrated in FIG. 1 and FIG. 2, a sanitary napkin 1 according to an embodiment of the present invention includes a liquid impermeable back sheet 2 formed of a polyethylene sheet, for example; a liquid permeable top sheet 3 that allows menstrual blood, vaginal discharge, and the like (hereinafter also collectively referred to as body fluids) to quickly pass through; and an absorbent body 4 interposed between the sheets 2 and 3 and made of cotton-like pulp or synthetic pulp, for example. Further, the sanitary napkin 1 includes a side non-woven fabric 7 provided over the substantially entire length of each side of a skin contact surface along a longitudinal direction, and also includes a polymer sheet 6 provided between the liquid permeable top sheet 3 and the absorbent body 4. At front and back end portions of the absorbent body 4, outer end portions of the liquid impermeable back sheet 2 and the liquid permeable top sheet 3 are bonded to each other with an adhesive such as a hot-melt adhesive or with an adhesive means such as a heat seal or an ultrasonic seal. Furthermore, at each side of the absorbent body 4, the liquid impermeable back sheet 2 and the side non-woven fabric that laterally extend longer than the absorbent body 4 are bonded to each other with an adhesive such as a hot-melt adhesive or with an adhesive means such as a heat seal and an ultrasonic seal. Further, wing-shaped flaps W, W projecting laterally are formed by layered sheet portions of the liquid impermeable back sheet 2 and the side non-woven fabric 7. Moreover, hip-holding flaps $W_B$, $W_B$ are formed on the buttocks side relative to the wing-shaped flaps W, W. The absorbent body 4 may be surrounded by an encapsulating sheet (not illustrated) made of a crepe paper sheet or a nonwoven fabric in order to retain a shape of the absorbent body 4 and to improve diffusivity thereof.

In the following, the structure of the sanitary napkin 1 will be described in more detail. The liquid impermeable back sheet 2 uses a sheet material such as polyethylene having at least a water shielding property. In addition, in terms of stuffiness prevention, a material having moisture permeability is preferably used. As such a water shielding and permeable sheet material, a microporous sheet is preferably used. The microporous sheet is obtained by forming a sheet by melting and kneading inorganic filler with olefin resin such as polyethylene and polypropylene, and subsequently stretching the sheet in one axial direction or two axial directions. On a non-skin side (an outer surface) of the liquid impermeable back sheet 2, one or more adhesive layers (not illustrated) are formed along the longitudinal direction of the napkin such that the sanitary napkin 1 is fixed to underwear when worn. As the liquid impermeable back sheet 2, a polyethylene laminate nonwoven fabric having a plastic film and a nonwoven fabric layered on each other may be used.

Next, as the liquid permeable top sheet 3, a perforated or an imperforated non-woven fabric, a porous plastic sheet, or the like is preferably used. Examples of a material fiber forming the non-woven fabric include synthetic fibers such as an olefin-based synthetic fiber such as polyethylene or polypropylene, a polyester-based synthetic fiber, and a polyamide-based synthetic fiber, regenerated fibers such as rayon and cuprammonium rayon, and natural fibers such as cotton. Further, as the liquid permeable top sheet 3, a nonwoven fabric obtained by applying an appropriate processing method such as a spunlace method, a spunbond method, a thermal bond method, a melt blown method, or a needle punch method to any of the above-described material fibers may be used. Among these processing methods, the spunlace method is superior in terms of flexibility, the spunbond method is superior in terms of drape properties, and the thermal bond method is superior in terms of bulkiness and compression restorability. When a plurality of through-holes is formed on the liquid permeable top sheet 3, body fluids can become quickly absorbed, providing a wearer with an excellent dry touch. Although either a long fiber or a short fiber may be used as the non-woven fabric, it is preferable to use a short fiber in order to provide texture of towel cloth. Further, in order to facilitate an embossing process, it is preferable to use an olefin-based fiber such as polyethylene or polypropylene having a relatively low melting point. Further, a composite fiber such as a core-in-sheath fiber having a high-melting-point fiber as a core and a low-melting-point fiber as a sheath, a side-by-side fiber, or a split fiber may be preferably used. A plurality of openings 11 is formed in a predetermined region of the liquid permeable top sheet 3, which will be described later in detail.

The absorbent body 4 interposed between the liquid impermeable back sheet 2 and the liquid permeable top sheet 3 is formed with, for example, cotton-like pulp and a water-absorptive polymer. The water-absorptive polymer is mixed, for example, as a granular powder, into the pulp forming the absorbent body. Examples of the pulp include chemical pulp made from wood, cellulose fibers such as dissolving pulp, and synthetic cellulose fibers such as rayon and acetate. In terms of function and price, softwood pulp with a long fiber length is more preferably used than hardwood pulp.

Further, a synthetic fiber may be mixed into the absorbent body 4. Examples of the synthetic fiber that may be used include polyolefin-based fibers such as polyethylene and polypropylene, polyester-based fibers such as polyethylene terephthalate and polybutylene terephthalate, polyamide-based fibers such as nylon, and a copolymer thereof. Also, a mixture of two types of the above-described fibers may be used. Further, a composite fiber such as a core-in-sheath fiber having a high-melting-point fiber as a core and a low-melting-point fiber as a sheath, a side-by-side fiber, or a split fiber may be used. In order to have hydrophilicity with body fluids, the synthetic fiber preferably undergoes surface treatment by using, for example, a hydrophilizing agent when a hydrophobic fiber is used.

As illustrated in FIG. 2, the polymer sheet 6 is disposed between the liquid permeable top sheet and the absorbent body 4, and the polymer sheet 6 includes highly absorbent resin disposed in predetermined regions between two nonwoven fabric sheets 6A, 6B. The polymer sheet 6 will be described later in detail.

As illustrated in the cross-sectional view of FIG. 2, a width dimension of the liquid permeable top sheet 3 is slightly larger than a width of the absorbent body 4 so as to cover the absorbent body 4. The side non-woven fabric 7, which is different from the liquid permeable top sheet 3, is provided outside the liquid permeable top sheet 3. To be more specific, the side non-woven fabric 7 formed of a nonwoven fabric material is provided to which appropriate water-repellency treatment or hydrophilic treatment is applied depending on the purpose such as preventing menstrual blood or vaginal discharge from permeating or enhancing texture. As the side non-woven fabric 7, a sheet that uses a synthetic fiber or a regenerated fiber as a material and is formed by an appropriate processing method may be used. Preferably, in order to prevent stuffiness while eliminating friction with the skin, a nonwoven fabric having air permeability with a reduced basis weight may be used as the side non-woven fabric 7. To be more specific, a nonwoven fabric with a basis weight of 13 to 23 $g/m^2$ is desirably used. Further, in order to securely prevent body fluids from permeating, a water-repellent nonwoven fabric coated with a silicon-based, a paraffin-based, or an alkyl-chromic-chloride-based water-repellent agent is preferably used.

As illustrated in FIG. 2, on each outer side of the sanitary napkin relative to its middle portion in a width direction, the side non-woven fabric 7 is bonded from an inward position of the absorbent body 4 slightly over a side edge of the absorbent body 4 to an outer edge of the liquid impermeable back sheet 2 with an adhesive such as a hot-melt adhesive. The layered sheet portions of the liquid impermeable back sheet 2 and each of the side non-woven fabric 7 form the pair of right and left wing-shaped flaps W, W that cover approximately the entire body fluid discharge region. Also, as illustrated in FIG. 1, the hip-holding flaps $W_B$, $W_B$ are formed on the buttocks side (backward side) relative to the wing-shaped flaps W, W. Outer surfaces of the wing-shaped flaps W, W and the hip-holding flaps $W_B$, $W_B$ each have an adhesive layer (not illustrated). When the sanitary napkin is attached to underwear, the wing-shaped flaps W, W are folded back at positions of fold-back lines RL so as to be fixed to a crotch portion of the underwear, and also the hip-holding flaps $W_B$, $W_B$ are fixed to an inner surface of the underwear. As illustrated in FIG. 2, an inner side of the side non-woven fabric 7 only covers the side edge of the absorbent body 4 and is bonded to the liquid permeable top sheet 3 with an adhesive such as a hot-melt adhesive.

[Space for Holding Body Fluids]

The sanitary napkin 1 is configured to form a space 10 for preventing body fluids with high viscosity such as thick viscous menstrual blood or coagulated and clotted menstrual blood (namely a clot of menstrual blood) from remaining on the surface when body fluids are excreted, while also holding the menstrual blood with high viscosity. The space 10 will be described below.

The liquid permeable top sheet 3 includes the plurality of openings 11 in a region corresponding to at least the body fluid discharge region H. The openings 11 are portions that pass through the liquid permeable top sheet 3 in a thickness direction and are not formed of a sheet member. Each of the openings 11 has a size that allows menstrual blood with high viscosity to pass through the liquid permeable top sheet 3.

Preferably, a range in which the openings 11 are formed is wider than the region corresponding to the body fluid discharge region H.

By forming the plurality of openings 11 in the region corresponding to the body fluid discharge region H, a clot of menstrual blood with high viscosity can pass through the liquid permeable top sheet 3 via the openings 11. Accordingly, the menstrual blood can be prevented from remaining on the surface.

Further, the sanitary napkin 1 includes the polymer sheet 6 disposed adjacent to a surface of an absorbent body 4 side of the liquid permeable top sheet 3, and the polymer sheet 6 includes highly absorbent resin disposed along the longitudinal direction on both sides of the region corresponding to the body fluid discharge region.

By disposing the polymer sheet 6 on the surface of the absorbent body 4 side of the liquid permeable top sheet 3, body fluids that have passed through the liquid permeable top sheet 3 come into direct contact with a surface of a skin side of the polymer sheet 6.

The polymer sheet 6 has a structure in which the highly absorbent resin is enclosed in predetermined regions between the upper layer nonwoven fabric 6A disposed on the skin side of the polymer sheet 6 and the lower layer nonwoven fabric 6B disposed on a non-skin side of the polymer sheet 6. Only the highly absorbent resin is disposed and no pulp is included between the nonwoven fabrics 6A and 6B. If pulp is included, the polymer sheet 6 before absorption becomes bulky. Thus, when the highly absorbent resin becomes swollen by absorption, the rate of increase in thickness may decrease, as compared to when only the highly absorbent resin is included.

As illustrated in FIG. 1 and FIG. 2, in the polymer sheet 6, highly absorbent resin regions 12 are formed along the longitudinal direction of the napkin on the both sides of the region corresponding to at least the body fluid discharge region H. At this time, the highly absorbent resin is enclosed inside by bonding portions that bond the upper layer nonwoven fabric 6A to the lower layer nonwoven fabric 6B. A region other than the highly absorbent resin regions 12 is a resin absence region in which the highly absorbent resin is not interposed. The region in which the highly absorbent is not interposed means that no highly absorbent resin is present between the upper layer nonwoven fabric 6A and the lower layer nonwoven fabric 6B, or means that highly absorbent resin is slightly present by, for example, entering between fibers when applied, but the amount of the highly absorbent resin is significantly smaller than that of the highly absorbent resin enclosed in each of the highly absorbent resin regions 12.

In the longitudinal direction of the sanitary napkin 1, the highly absorbent resin regions 12 may at least include the region corresponding to the body fluid discharge region H, and preferably, the highly absorbent resin regions 12 extend longer than the region corresponding to the body fluid discharge region H in a front-back direction. In the example illustrated in FIG. 1, the highly absorbent resin regions 12 each have the approximately same length as a longitudinal length of a base edge portion of the wing-shaped flap W. Between the right and left highly absorbent resin regions 12, the highly absorbent resin is not present and the upper layer nonwoven fabric 6A and the lower layer nonwoven fabric 6B are only present.

In the highly absorbent resin regions 12 and in their vicinity, the upper layer nonwoven fabric 6A and the lower layer nonwoven fabric 6B are not bonded to each other, and in a region other than the highly absorbent resin regions 12 and in their vicinity, the upper layer nonwoven fabric 6A and the lower layer nonwoven fabric 6B are bonded to each other. The bonding portion between the upper layer nonwoven fabric 6A and the lower layer nonwoven fabric 6B may be disposed such that the highly absorbent resin is enclosed in the highly absorbent resin regions 12 or such that the region other than the highly absorbent resin regions 12 may be entirely bonded.

The polymer sheet 6 may be formed with a size that extends slightly outward from the highly absorbent resin regions 12 and that at least covers the body fluid discharge region H of the wearer and its vicinity. In the width direction of the sanitary napkin 1, the polymer sheet 6 preferably has a width approximately equal to a width of the absorbent body 4. Further, in the longitudinal direction of the sanitary napkin 1, the polymer sheet 6 preferably has a length slightly longer than the length of the base edge portion of the wing-shaped flap W in the front-back direction, or has the same length as that of the absorbent body 4.

The polymer sheet 6 is disposed in the region corresponding to at least the body fluid discharge region H of the wearer. The sanitary napkin illustrated in FIG. 1 is a nighttime sanitary napkin having a longer back side so as to cover the buttock of the wearer. Therefore, the polymer sheet 6 is disposed at a position closer to the front side of the sanitary napkin 1. In a case where the sanitary napkin 1 is a daytime sanitary napkin that covers body fluid discharge region H and its vicinity, the polymer sheet 6 is preferably disposed in the center of the sanitary napkin 1.

Figure 3:
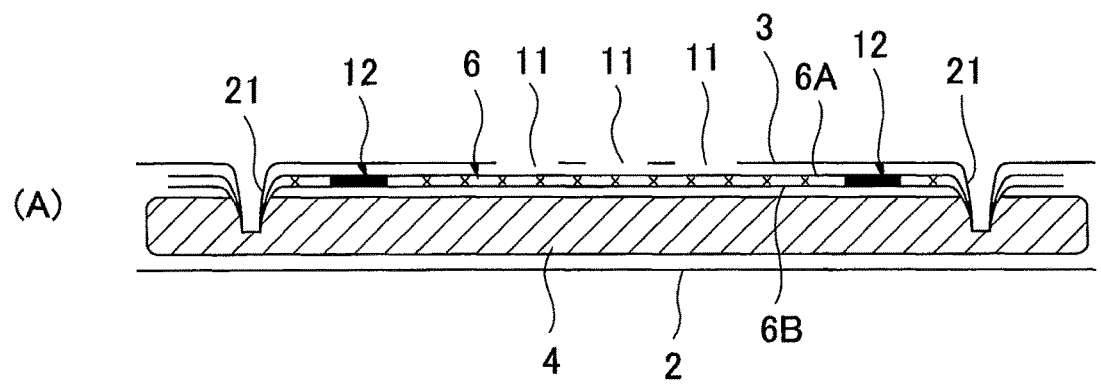
Figure 3:
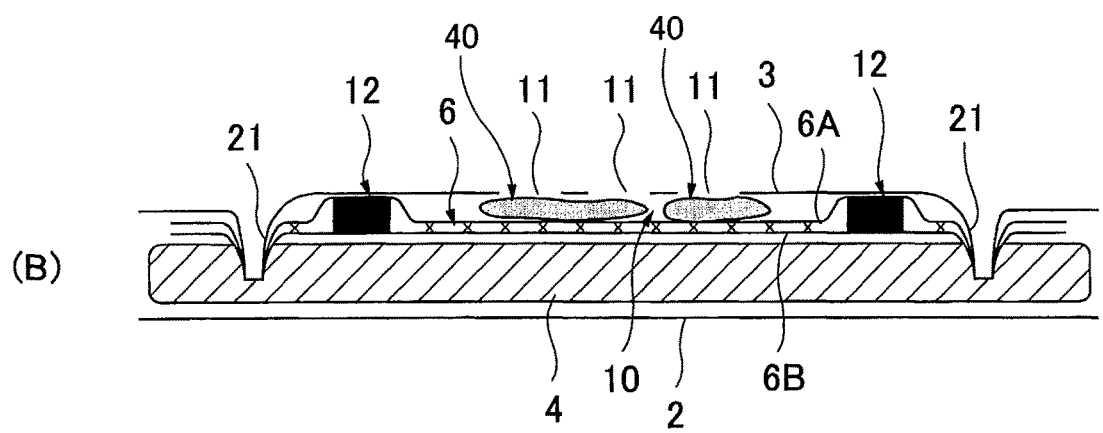

As illustrated in FIG. 3, when the highly absorbent resin becomes swollen by absorption, the space 10 for holding a body fluid is formed between the highly absorbent resin regions 12 and also between the liquid permeable top sheet 3 and the polymer sheet 6. The space 10 is a gap portion between the liquid permeable top sheet 3 and the polymer sheet 6 (the upper layer nonwoven fabric 6A). The gap portion is formed when the liquid permeable top sheet 3, located between the highly absorbent resin regions 12, is raised toward the skin side, accompanied by the highly absorbent resin disposed in the right and left regions 12 becoming swollen by absorption and protruding toward the skin side.

As the space 10 is formed when the highly absorbent resin disposed in the regions 12 becomes swollen by absorption, menstrual blood 40 with high viscosity that has passed through the liquid permeable top sheet 3 via the openings 11 can be held in the space 10, as illustrated in FIG. 3(B). Accordingly, it is possible to prevent the menstrual blood 40 with high viscosity from coming into direct contact with the skin and reduce discomfort when the sanitary napkin is worn. Further, in a case where body pressure is applied with the menstrual blood 40 with high viscosity being held in the space 10, the highly absorbent resin regions 12 can suppress compressive force applied to the menstrual blood 40 with high viscosity. Accordingly, it is possible to prevent the menstrual blood 40 with high viscosity from returning back to the surface. Further, the space 10 is formed when the highly absorbent resin becomes swollen by absorption of excreted body fluids, and the surface is approximately flat before excretion as illustrated in FIG. 3(A). Therefore, the wearability of the sanitary napkin 1 before excretion remains the same as that of a typical absorbent article.

A separation distance (a distance in the width direction of the napkin) between the right and left highly absorbent resin regions 12 is 15 to 50 mm, and is preferably 15 to 30 mm. With the separation distance of less than 15 mm, the body fluid discharge region of the wearer is not readily located between the right and left highly absorbent resin regions 12, and thus excreted fluids may flow to the outside of the highly absorbent resin regions 12. Also, with the separation distance of greater than 50 mm, when the highly absorbent resin becomes swollen by absorption and protrudes toward the skin side, the liquid permeable top sheet 3 located between the right and left highly absorbent resin regions 12 is loosed and is thus not readily raised toward the skin side. As a result, the space 10 is not readily formed.

The length of each of the highly absorbent resin regions 12 in the longitudinal direction is preferably approximately 30 to 50 mm from the center of the body fluid discharge region H toward the front side and is approximately 30 to 50 mm toward the back side. The length from the center of the body fluid discharge region H toward the front side may be the same as or may be different from the length from the center of the body fluid discharge region H toward the back side. When the length from the center of the body fluid discharge region H toward the back side is greater than 50 mm, body fluids may be excessively diffused to the back side, which may cause the body fluids to leak.

Figure 4:
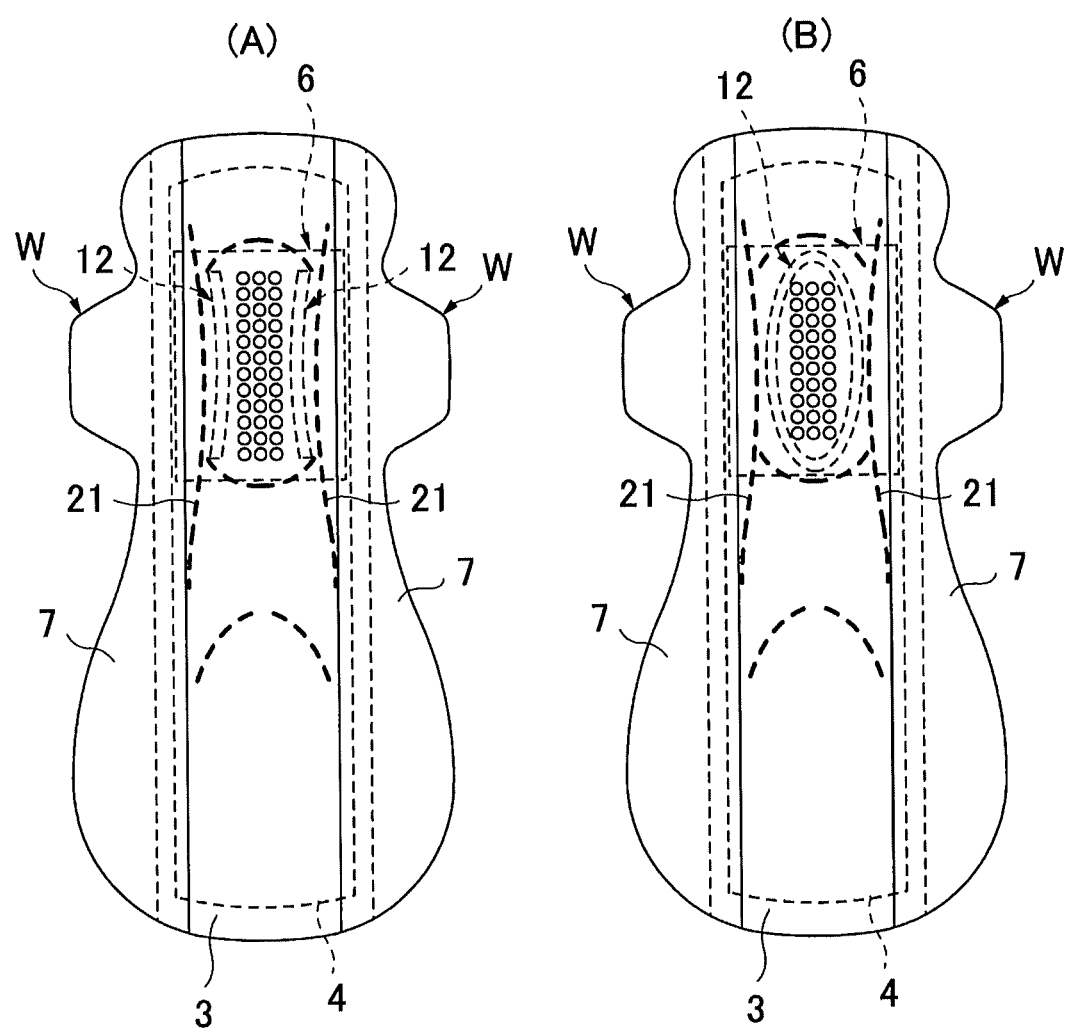
FIGS. 4(A) and (B) are planar views of the sanitary napkin 1 illustrating variation examples of highly absorbent resin regions 12.

As illustrated in FIG. 1, the highly absorbent resin regions 12 can be disposed linearly (in a belt-like shape) along the longitudinal direction of the napkin on the respective sides of the body fluid discharge region H so as to be spaced apart from each other in the width direction of the napkin. Further, as illustrated in FIG. 4(A), the highly absorbent resin regions 12 may be disposed in a curved form that curves inward or outward (inward in the illustrated example) in the width direction. Further, as illustrated in FIG. 4(B), the highly absorbent resin regions 12 may be disposed in an elliptical shape, a circular shape, a diamond shape, or a polygonal shape (an elliptical shape in the illustrated example) by connecting the front ends and the rear ends of the right and left highly absorbent resin regions 12 so as to surround the periphery of the body fluid discharge region H by a closed shape.

Typically, a clot of menstrual blood with high viscosity has a size of 2 to 10 mm. Thus, a size of each of the openings 11 is 3 to 15 mm and is preferably 4 to 10 mm such that the clot of menstrual blood with high viscosity can pass through. When the size of each of the openings 11 is less than 3 mm, a clot of menstrual blood with high viscosity does not readily pass through the liquid permeable top sheet 3. As a result, the menstrual blood remains on the surface and discomfort is caused when the sanitary napkin is worn. Further, when the size of each of the openings 11 is greater than 15 mm, while a clot of menstrual blood with high viscosity can readily pass through the liquid permeable top sheet 3, body fluids held in the space 10 may easily return back to the surface via the openings 11. As a result, discomfort may be caused when the sanitary napkin is worn.

A separation distance between the adjacent openings 11 is preferably approximately 2 to 8 mm such that the menstrual blood 40 with high viscosity can readily pass through the openings 11 and also the menstrual blood 40 returning back to the surface can be reduced as much as possible. When the size of each of the openings 11 is less than 2 mm, the strength of the nonwoven fabric becomes insufficient and thus the nonwoven fabric may be cut during manufacturing or during use. When the size is greater than 8 mm, the menstrual blood 40 with high viscosity does not readily pass through the openings 11 as a non-opening portion area is large.

As illustrated in FIG. 1, an arrangement pattern of the openings 11 may be a lattice pattern in which the openings 11 are aligned in the longitudinal direction and in the width direction of the sanitary napkin 1 or may be a zigzag pattern in which adjacent columns and rows are shifted by a half pitch in the longitudinal direction or in the width direction of the sanitary napkin 1. As illustrated in FIG. 1, it is desirable to arrange the openings 11 in a plurality of columns, preferably in two to five columns, along the longitudinal direction of the sanitary napkin 1. In the illustrated example, the openings 11 are arranged in three columns along the longitudinal direction of the sanitary napkin 1.

Each of the openings 11 may be a circular shape in planar view as in the illustrated examples, or may be an elliptical shape or a polygonal shape in planar view, although not illustrated. Similarly to an elliptical shape, when the shape of each of the openings 11 has a major axis direction and a minor axis direction, the longitudinal direction of the napkin is preferably set as the major axis direction and the length in the minor axis direction is preferably 3 to 15 mm.

The openings 11 are preferably formed between the right and left regions 12 having the highly absorbent resin of the polymer sheet 6 and also formed in a longitudinal range of the highly absorbent resin regions 12. Accordingly, the menstrual blood 40 with high viscosity that has passed through the openings 11 can be securely held in the space 10 formed upon absorption of excreted body fluids. Further, the openings 11 may be formed outside the highly absorbent resin regions 12 as desired.

As a means of forming the openings 11 on the liquid permeable top sheet 3, any one of the following three means is preferably used. As a first means, as illustrated in FIG. 1 and FIG. 2, the liquid permeable top sheet 3 can be formed of a single sheet having the plurality of openings 11 in the region corresponding to the body fluid discharge region H. When the liquid permeable top sheet 3 is formed of the single sheet, the number of components can be reduced and thus a manufacturing process can be simplified. In order to form the openings 11 on the liquid permeable top sheet 3, the liquid permeable top sheet 3 may be punched by a punching method or pierced by pins.

Figure 5:
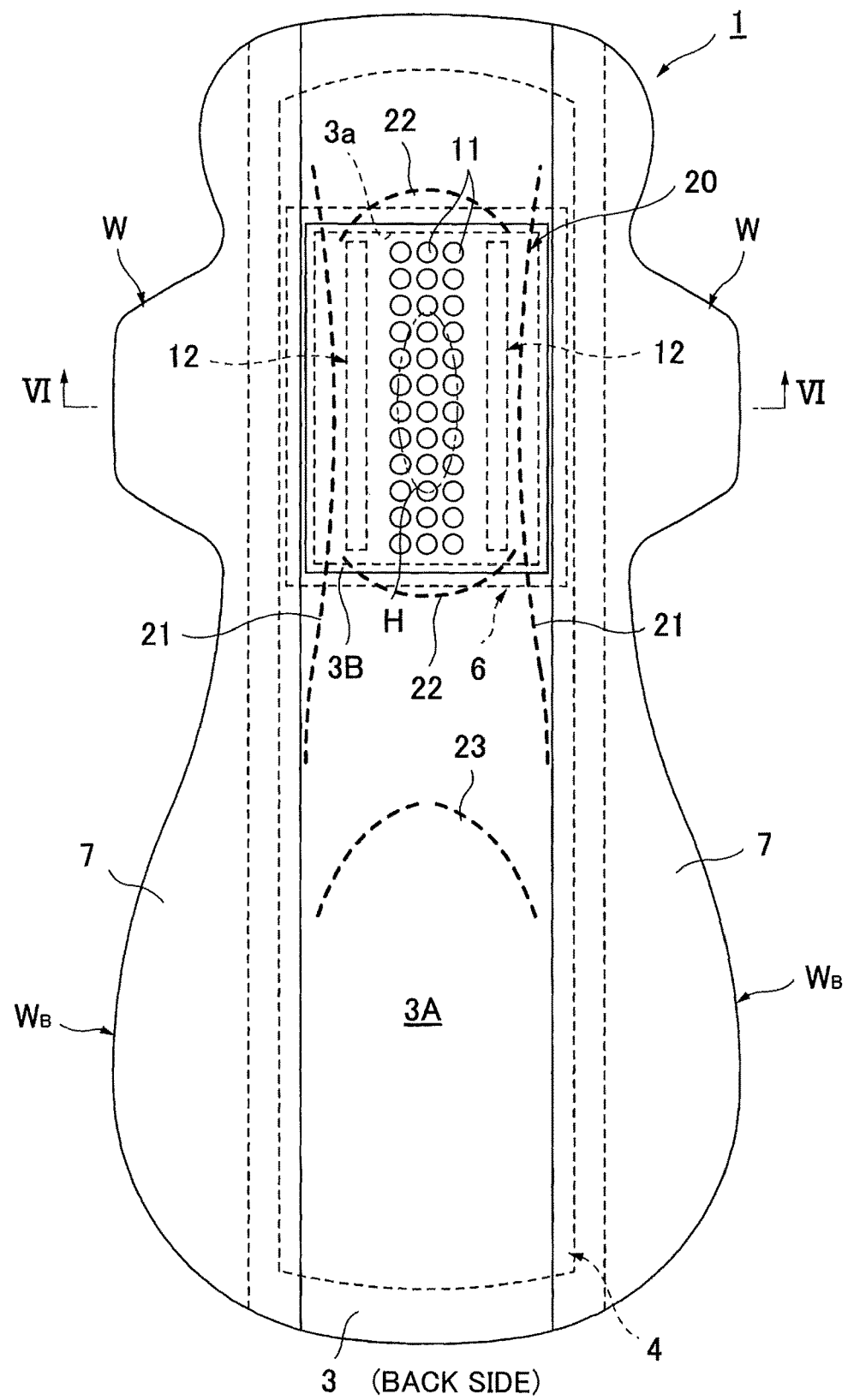
FIG. 5 is an expanded view of a sanitary napkin 1 according to a variation example.
Figure 6:
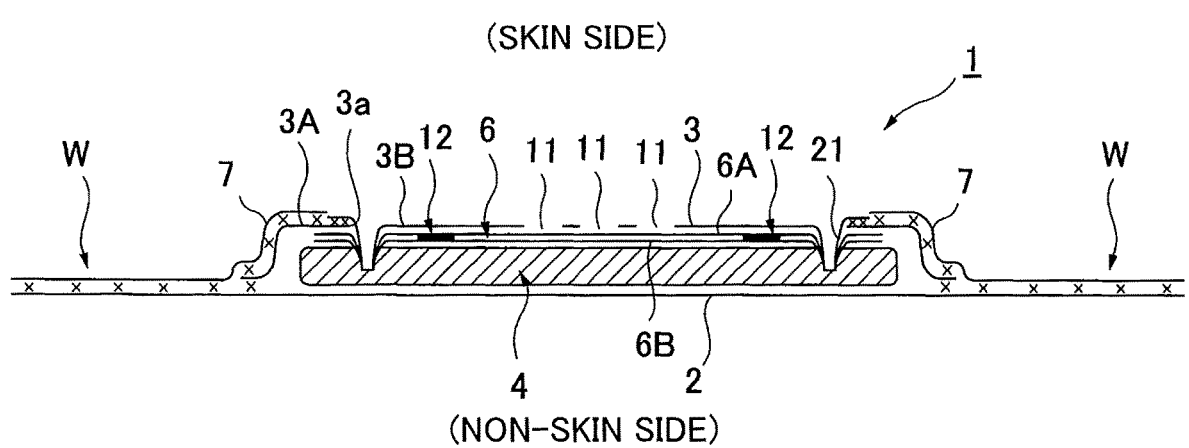
FIG. 6 is a cross-sectional view taken along a line VI-VI of FIG. 5.

As a second means, as illustrated in FIG. 5 and FIG. 6, the liquid permeable top sheet 3 can be formed of a composite sheet. The composite sheet includes a substrate sheet 3A having, as a region corresponding to the body fluid discharge region H, a pass-through portion 3a through which a body fluid passes in the thickness direction and also includes a perforated sheet 3B that has the plurality of openings 11 and is bonded to the pass-through portion 3a. In this configuration, because the perforated sheet 3B is bonded to the substrate sheet 3A, a commercially available sheet on which openings are preliminarily formed can be used, and thus an opening forming process is not required.

Figure 9:
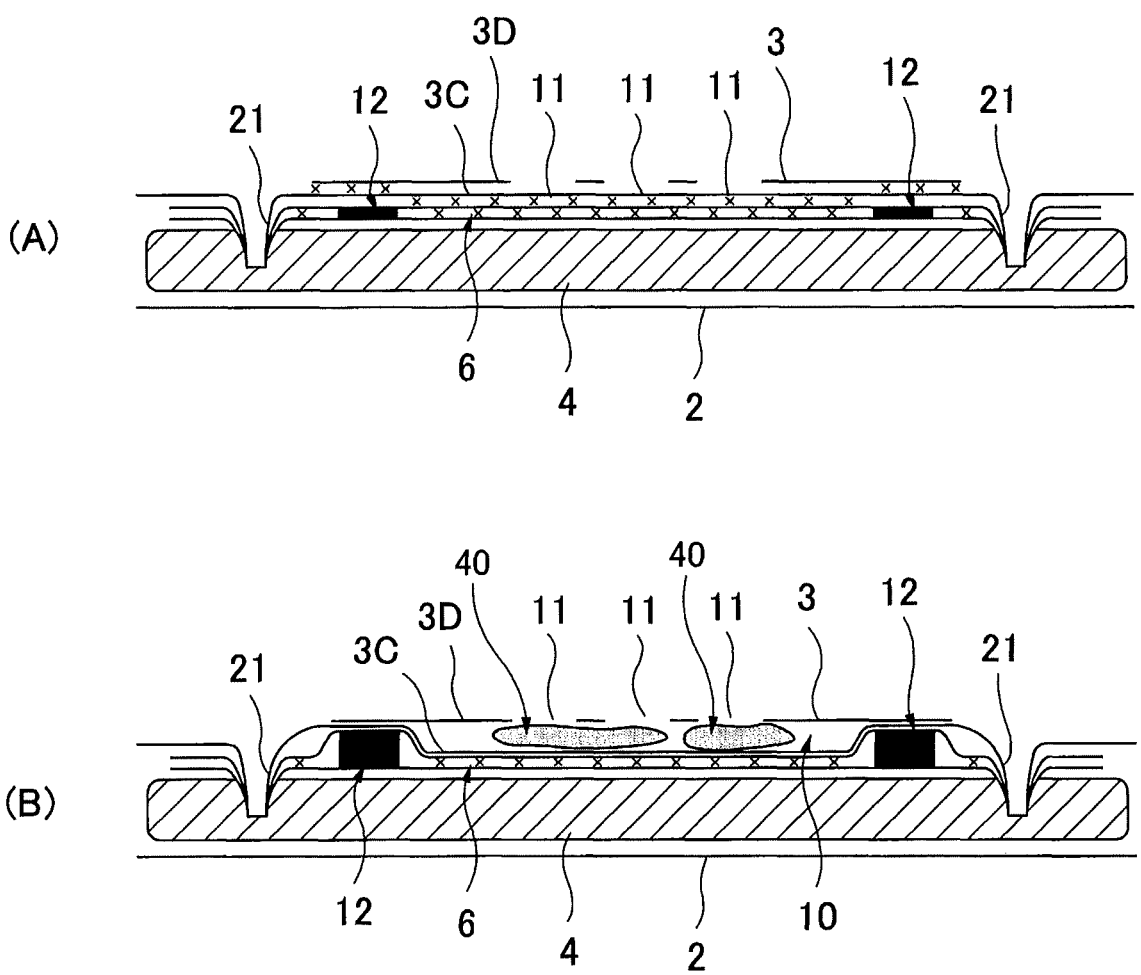

As a third means, as illustrated in FIG. 9A, the liquid permeable top sheet 3 can include a layered sheet. The layered sheet includes a substrate sheet 3C formed as a uniform sheet without the pass-through portion 3a and also includes a perforated sheet 3D that has the plurality of openings 11 and is layered in the region corresponding to the body fluid discharge region H of the substrate sheet 3C. At this time, the perforated sheet 3D is not bonded to the substrate sheet 3C between the highly absorbent resin regions 12 of the polymer sheet 6. The perforated sheet 3D is bonded to outer peripheral sides of the substrate sheet 3C relative to the highly absorbent resin regions 12. Further, the substrate sheet 3C is bonded to the polymer sheet 6 between the highly absorbent resin regions 12. Accordingly, when the highly absorbent resin of the polymer sheet 6 becomes swollen by absorption, only the perforated sheet 3D is raised and the space 10 is formed between the perforated sheet 3D and the substrate sheet 3C, as illustrated in FIG. 9(B).

Next, as illustrated in FIG. 1, in the sanitary napkin 1, a compressed groove 20 that is recessed from the outer surface side of the liquid permeable top sheet 3 toward the liquid impermeable back sheet 2 is formed along the longitudinal direction on each of the sides of the region corresponding to the body fluid discharge region H. As illustrated in FIG. 1 and FIG. 2, the compressed groove 20 is formed in such a manner that components located from the liquid permeable top sheet 3 to the absorbent body 4 are integrally formed by compression from the outer surface side of the liquid permeable top sheet 3. The compressed groove 20 includes both-sides compressed grooves 21 disposed along the longitudinal direction on the both sides of the region corresponding to the body fluid discharge region H. In the illustrated example, front and rear compressed grooves 22 disposed on the front and rear sides of the region corresponding to the body fluid discharge region H are formed. Also, a rearward compressed groove 23 curved toward the front side is formed along the width direction on the buttocks side relative to the front and rear compressed grooves 22. The both-sides compressed grooves 21 and the front and rear compressed grooves 22 are disposed to substantially surround the region corresponding to the body fluid discharge region H in a circumferential direction.

In the sanitary napkin 1 including the above-described compressed groove 20, the highly absorbent resin regions 12 are preferably disposed between the both-sides compressed grooves 21 in the width direction of the sanitary napkin 1. Accordingly, as illustrated in FIG. 3(B), when the highly absorbent resin becomes swollen by absorption and protrudes toward the skin side, the space 10 is securely formed between the highly absorbent resin regions 12 without preventing the liquid permeable top sheet 3 from being raised toward the skin side.

Further, in the longitudinal direction of the sanitary napkin 1, the highly absorbent resin regions 12 are preferably disposed between the front and rear compressed grooves 22. Accordingly, similarly to the above, the space 10 is securely formed between the highly absorbent resin regions 12. As illustrated in FIG. 1 and FIG. 2, the upper layer nonwoven fabric 6A and the lower layer nonwoven fabric 6B of the polymer sheet 6 preferably have a size so as to overlap the both-sides compressed grooves 21 and the front and rear compressed grooves 22, and are also preferably compressed integrally with the liquid permeable top sheet 3 and the absorbent body 4 when the compressed grooves 21 and 22 are formed. Accordingly, the position of the polymer sheet 6 can be prevented from shifting when the sanitary napkin 1 is worn, and also the space 10 is securely formed in the region corresponding to the body fluid discharge region H when the highly absorbent resin becomes swollen by absorption.

Figure 7:
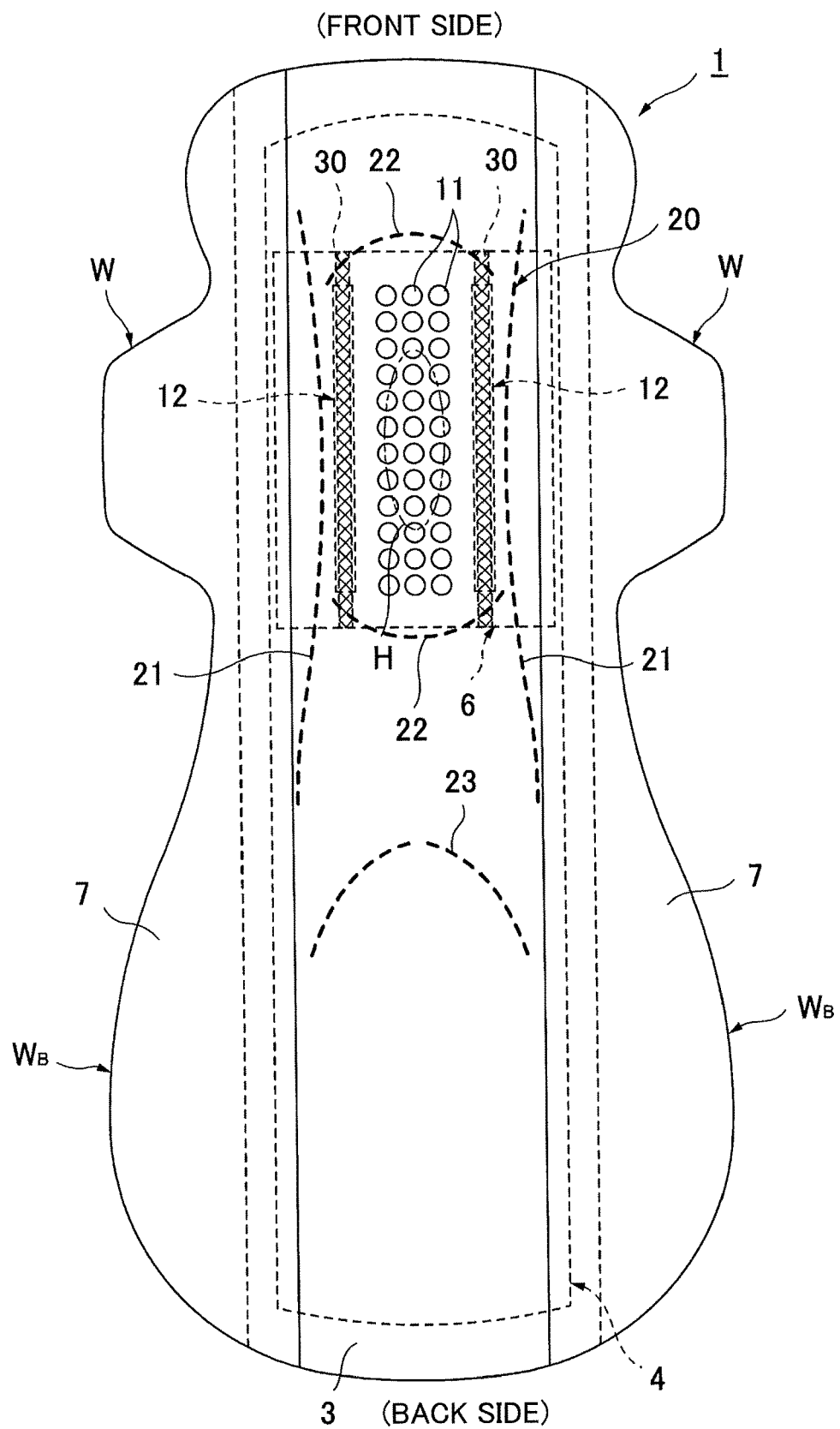
FIG. 7 is an expanded view of a sanitary napkin 1 according to a variation example.
Figure 8:
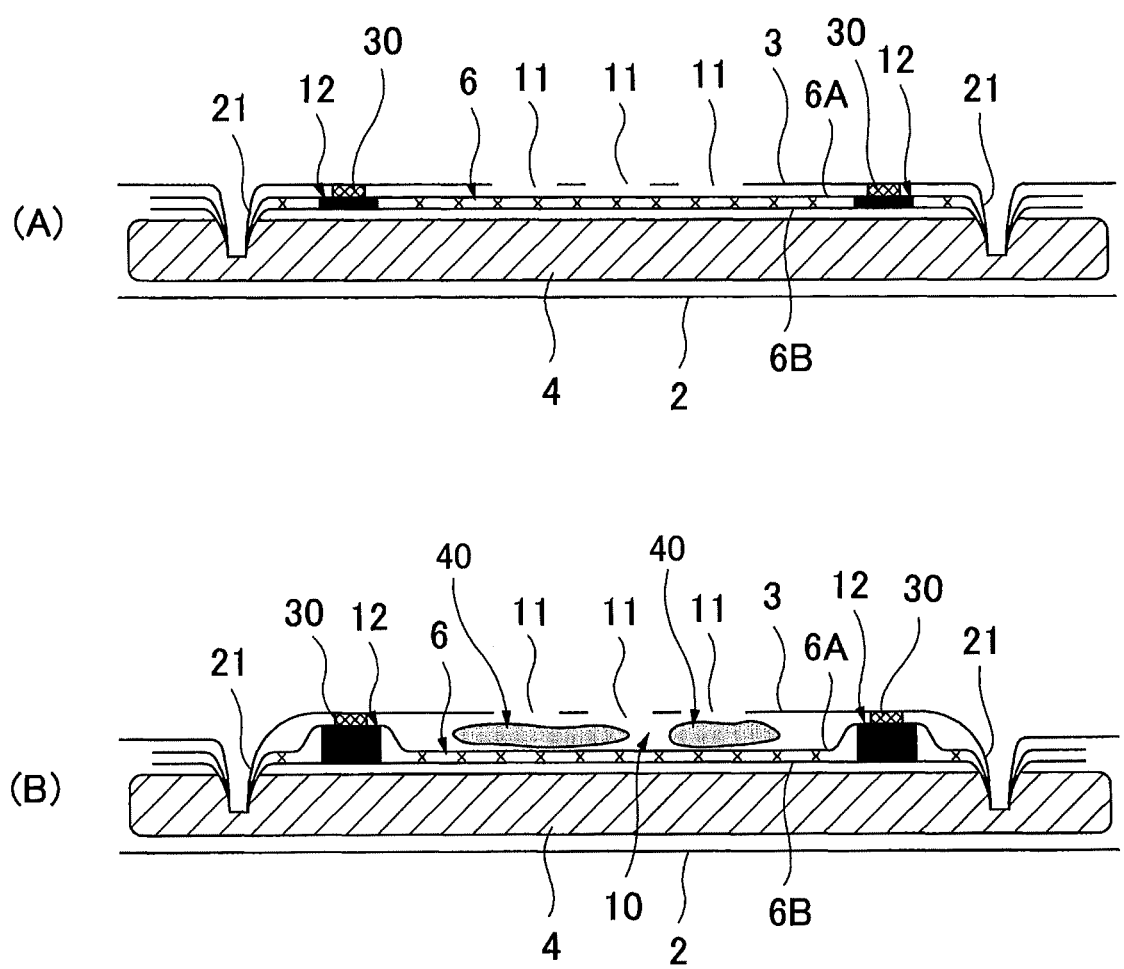

Next, bonding of the liquid permeable top sheet 3 to the polymer sheet 6 will be described. As illustrated in FIG. 7 and FIG. 8(A), the liquid permeable top sheet 3 and the polymer sheet 6 are preferably bonded to each other at adhesion portions 30. The adhesion portions 30 are each formed in a linear shape or a belt-like shape over the approximate entire length of the polymer sheet 6 along the longitudinal direction passing at least a portion that overlaps with each of the highly absorbent resin regions 12. Accordingly, as illustrated in FIG. 8B, the liquid permeable top sheet 3 between the highly absorbent resin regions 12 can be readily raised toward the skin side when the highly absorbent resin becomes swollen by absorption and protrudes toward the skin side. Thus, the space can be securely formed between the liquid permeable top sheet 3 and the polymer sheet 6. Further, the adhesion portions 30 may be provided within a range that does not prevent formation of the space 10. However, the adhesion portions 30 are desirably provided by avoiding the openings 11 because an adhesive may flow out of the openings 11 to the surface.

The adhesion portions 30 are portions to which an adhesive such as a hot-melt adhesive is intermittently applied by a spiral, a spray, or a dot method in such a manner that does not prevent body fluids from permeating.

Further, an adhesion region where the polymer sheet 6 adheres to the absorbent body 4 is preferably a region other than a region where the openings 11 of the liquid permeable top sheet 3 are formed. Because large amounts of body fluids pass through the region where the openings 11 of the liquid permeable top sheet 3 are formed, it is preferable to cause the body fluids to pass through the region toward the absorbent body 4 as quickly as possible. Therefore, in the region where the openings are formed, it is preferable not to provide the adhesion region, which may prevent body fluids from passing through.

Moreover, the upper layer nonwoven fabric 6A of the polymer sheet 6 preferably includes a means for allowing the highly absorbent resin regions 12 to readily protrude toward the skin side when the highly absorbent resin becomes swollen by absorption. As such a means, the highly absorbent resin regions 12 of the upper layer nonwoven fabric 6A may have loosened portions that are loosened in the width direction, or the upper layer nonwoven fabric 6A may be formed of a material having elasticity higher than that of the lower layer nonwoven fabric 6B.

In the following, various aspects of the embodiments of the present invention will be added.

(Clause 1)

According to a first aspect, there is provision of an absorbent article having an absorbent body interposed between a liquid permeable top sheet and a back sheet, wherein a plurality of openings is formed in a region corresponding to at least a body fluid discharge region of the liquid permeable top sheet, a polymer sheet is disposed adjacent to a surface on an absorbent body side of the liquid permeable top sheet and the polymer sheet includes highly absorbent resin disposed along a longitudinal direction on both sides of the region corresponding to the body fluid discharge region, and when the highly absorbent resin becomes swollen by absorption, a space for holding a body fluid is formed between regions in which the highly absorbent resin is disposed and also between the liquid permeable top sheet and the polymer sheet.

According to the first aspect, as the liquid permeable top sheet, a sheet having a plurality of openings formed in a region corresponding to a body fluid discharge region is used. Therefore, even a clot of menstrual blood with high viscosity can pass through the liquid permeable top sheet via the openings. It is thus possible to prevent body fluids from remaining on the surface. Further, the absorbent article includes the polymer sheet disposed adjacent to the surface on the absorbent body side of the liquid permeable top sheet, and the polymer sheet includes the highly absorbent resin disposed along the longitudinal direction on the both sides of the region corresponding to the body fluid discharge region. When the highly absorbent resin becomes swollen by absorption, the liquid permeable top sheet is raised toward a skin side of the liquid permeable top sheet between the regions in which the highly absorbent resin is disposed. As a result, the space for holding a body fluid is formed between the regions in which the highly absorbent resin is disposed and also between the liquid permeable top sheet and the polymer sheet. Accordingly, the menstrual blood with high viscosity that has passed through the liquid permeable top sheet via the openings can be held in this space, and thus the menstrual blood with high viscosity does not come into direct contact with the skin. As a result, discomfort when the absorbent article is worn can be reduced. Further, even when body pressure is applied while the menstrual blood with high viscosity is held in the space, the regions disposed on the both sides and having the highly absorbent, swollen resin can suppress compressive force applied to the menstrual blood with high viscosity. It is thus possible to prevent the menstrual blood with high viscosity from returning back to the surface. The space is formed when the highly absorbent resin becomes swollen by absorption of excreted body fluids, and the surface is approximately flat before excretion. Thus, wearability before excretion is the same as that of a typical absorbent article.

(Clause 2)

According to a second aspect, the absorbent article is provided, wherein the liquid permeable top sheet and the polymer sheet are not bonded to each other between the regions in which the highly absorbent resin is disposed.

According to the above-described second aspect, the liquid permeable top sheet and the polymer sheet are not bonded to each other between the regions in which the highly absorbent resin is disposed. Therefore, when the highly absorbent resin becomes swollen by absorption, only the liquid permeable top sheet is raised toward the skin side and thus the space is securely formed.

As a third aspect, the absorbent article according to claim 1 or claim 2 is provided, wherein compressed grooves that are recessed from an outer surface side of the liquid permeable top sheet toward the back sheet are formed along the longitudinal direction on the both sides of the region corresponding to the body fluid discharge region, and the regions in which the highly absorbent resin is disposed are positioned between the compressed grooves.

In the third aspect, when the compressed grooves are formed along the longitudinal direction on the both sides of the region corresponding to the body fluid discharge region, the regions in which the highly absorbent resin is disposed are positioned between the right and left compressed grooves. Accordingly, when the highly absorbent resin becomes swollen by absorption, the compressed grooves do not prevent the liquid permeable top sheet from being raised toward the skin side, and thus the space can be securely formed.

As a fourth aspect, the absorbent article according to any one of claims 1 to 3 is provided, wherein a separation distance between the regions in which the highly absorbent resin is disposed is 15 to 50 mm.

In the above-described fourth aspect, the space has a size that allows the menstrual blood with high viscosity to be securely held. Therefore, the separation distance between the regions in which the highly absorbent resin is disposed is set in a predetermined range.

As a fifth aspect, the absorbent article according to any one of claims 1 to 4 is provided, wherein a size of each of the openings is 3 to 15 mm.

In the above-described fifth aspect, the openings has the predetermined size such that the menstrual blood with high viscosity can securely pass through the liquid permeable top sheet without remaining on the surface, while also the body fluids held in the space can be prevented from returning back to the surface side.

As a sixth aspect, the absorbent article according to any one of claims 1 to 5 is provided, wherein the liquid permeable top sheet is formed of: a single sheet having a plurality of openings in a region corresponding to a body fluid discharge region; a composite sheet including a substrate sheet having, as a region corresponding to a body fluid discharge region, a pass-through portion through which the body fluid passes in a thickness direction and also including a perforated sheet that has a plurality of openings and is bonded to the pass-through portion; or a layered sheet including a perforated sheet that has a plurality of openings and is layered in a region corresponding to a body fluid discharge region of a substrate sheet.

In the above-described sixth aspect, as a means for forming the plurality of openings in the region corresponding to the body fluid discharge region of the liquid permeable top sheet, the liquid permeable top sheet is formed of: the single sheet having the plurality of openings in the region corresponding to the body fluid discharge region; the composite sheet including the substrate sheet having, as the region corresponding to the body fluid discharge region, the pass-through portion through which the body fluid passes in the thickness direction and also including the perforated sheet that has the plurality of openings and is bonded to the pass-through portion; or the layered sheet including the perforated sheet that has the plurality of openings and is layered in the region corresponding to the body fluid discharge region of the substrate sheet. When the liquid permeable top sheet is formed of the single sheet, the number of components can be reduced and a manufacturing process can be simplified. Conversely, when the liquid permeable top sheet is formed of the composite sheet, a commercially available sheet on which openings are formed can be used, and thus an opening forming process is not required. When the liquid permeable top sheet is formed of the layered sheet, by bonding the substrate sheet to the polymer sheet, only the perforated sheet is raised when the highly absorbent resin becomes swollen by absorption. Accordingly, a space can be formed between the perforated sheet and the substrate sheet.

Although the present invention has been described according to the embodiments, the present invention is not limited to the above-discussed embodiments, and various modifications may be made without departing from the scope of the present invention.

The present application is based on Japanese priority application No. 2016-64239 filed on Mar. 28, 2016, with the Japanese Patent Office, the entire contents of which are hereby incorporated by reference.

DESCRIPTION OF THE REFERENCE NUMERAL 1 sanitary napkin
2 liquid impermeable back sheet
3 liquid permeable top sheet
4 absorbent body
6 polymer sheet
6A upper layer nonwoven fabric
6B lower layer nonwoven fabric
7 side non-woven fabric
10 space
11 openings
12 highly absorbent resin regions
20 compressed groove
21 both-sides compressed grooves
22 front and rear compressed grooves
30 adhesion portion
40 menstrual blood with high viscosity

The invention claimed is:

1. An absorbent article comprising:
   a liquid permeable top sheet including a plurality of openings in a region corresponding to at least a body fluid discharge region;
   a back sheet;
   an absorbent body provided between the liquid permeable top sheet and the back sheet; and
   a polymer sheet disposed adjacent to a surface of an absorbent body side of the liquid permeable top sheet, the polymer sheet including two regions of highly absorbent resin disposed along a longitudinal direction at only respective ends on both sides of the region corresponding to the body fluid discharge region,
   wherein, before the highly absorbent resin becomes swollen, a surface of the polymer sheet is formed flat,
   wherein, upon the highly absorbent resin becoming swollen by absorption and raised toward a skin side, the liquid permeable top sheet located between disposed regions of the highly absorbent resin is raised toward the skin side, and thereby, a space for holding a body fluid is formed between regions in which the highly absorbent resin is disposed and also between the liquid permeable top sheet and the polymer sheet.

2. The absorbent article according to claim 1, wherein the liquid permeable top sheet and the polymer sheet are not bonded to each other between the regions in which the highly absorbent resin is disposed.

3. The absorbent article according to claim 1, wherein compressed grooves that are recessed from an outer surface side of the liquid permeable top sheet toward the back sheet are formed along the longitudinal direction on the respective sides of the region corresponding to the body fluid discharge region, and the regions in which the highly absorbent resin is disposed are located between the compressed grooves.

4. The absorbent article according to claim 1, wherein a separation distance between the regions in which the highly absorbent resin is disposed is 15 to 50 mm.

5. The absorbent article according to claim 1, wherein a size of each of the openings is 3 to 15 min.

6. The absorbent article according to claim 1, wherein the liquid permeable top sheet is formed of: a single sheet having a plurality of openings in a region corresponding to a body fluid discharge region; a composite sheet including a substrate sheet having, as a region corresponding to a body fluid discharge region, a pass-through portion through which the body fluid passes in a thickness direction and also including a perforated sheet that has a plurality of openings and is bonded to the pass-through portion, or a layered sheet including a perforated sheet that has a plurality of openings and is layered in a region corresponding to a body fluid discharge region of a substrate sheet.

* * * * *